US00PP12825P2

(12) United States Plant Patent

Olesen et al.

(10) Patent No.: US PP12,825 P2

(45) Date of Patent: Aug. 6, 2002

(54) SHRUB ROSE PLANT NAMED 'POULISAB'

(76) Inventors: L. Pernille Olesen; Mogens N. Olesen, both of Hillerødvejen 49, DK-3480 Fredensborg (DK)

( * ) Notice: Subject to any disclaimer, the term of this patent is extended or adjusted under 35 U.S.C. 154(b) by 0 days.

(21) Appl. No.: 09/270,177

(22) Filed: Mar. 15, 1999

(51) Int. Cl.[7] ..... A01H 5/00

(52) U.S. Cl. ..... Plt./108

(58) Field of Search ..... Plt./139, 140, 108, Plt./150, 151

(56) References Cited

U.S. PATENT DOCUMENTS

PP6,264 P * 8/1988 Olesen et al. ..... Plt./139

OTHER PUBLICATIONS

UPOV–ROM, 2001/01, Plant Variety Database, GTI Jouve Retrieval Software, citation for 'POULisab'.*

UPOV–ROM, 2000/04, Plant Variety Database, GTI Jouve Retrieval Software, citation for 'POULisab'.*

Canadian Food Inspection Agency "Applications Accepted for Filing" 1 page Apr. 1998 Canada.

Community Plant Variety Office "Certificate On The Grant . . . " 6 pages Jul. 20, 1998 EU.

* cited by examiner

*Primary Examiner*—Howard J. Locker

(57) ABSTRACT

A new garden rose plant which has abundant, deep red flowers, fragrance, and attractive foliage. This new and distinct variety has shown to be uniform and stable in the resulting generations from asexual propagation.

1 Drawing Sheet

SUMMARY OF THE INVENTION

The present invention constitutes a new and distinct variety of garden rose plant which originated from a controlled crossing between an unnamed seedling and 'POULnorm' (U.S. Plant patent application Ser. No. 09/276,892). The two parents were crossed and the resulting seeds were planted in a controlled environment. The new variety is named 'POULisab'.

The new rose may be distinguished from its seed parent, an unnamed seedling, by the following combination of characteristics:

1. The seed parent is a floribunda, whereas 'POULisab' is a shrub.

2. The seed parent has a light fragrance, where 'POULisab' has a strong fragrance.

3. The plant habit of the seed parent is lower and bushier than 'POULisab'.

The new variety may be distinguished from its pollen parent, 'POULnorm' (U.S. Plant patent application Ser. No. 09/276,892, dated Mar. 25, 1999), created by the same inventors, by the following combination of characteristic:

1. The pollen parent is a climbing rose and is much taller than 'POULisab'.

2. 'POULnorm' has a narrower growth habit than that of 'POULisab'.

The objective of the hybridization of this rose variety for nursery and garden use was to create a new and distinct variety with unique qualities, such as:

1. Uniform and abundant flowers;

2. Vigorous, compact growth;

3. Exceptional fragrance;

4. Disease Resistance.

This combination of qualities is not present in previously available commercial cultivars of this type and distinguish 'POULisab' from all other varieties of which we are aware.

As part of their rose development program, L. Pernille Olesen and Mogens N. Olesen germinated the seeds from the aforementioned hybridization and conducted evaluations on the resulting seedlings in a controlled environment in Fredensborg, Denmark.

'POULisab' was selected in the spring of 1991 by the inventors as a single plant from the aforementioned hybridization.

Asexual reproduction of 'POULisab' by traditional budding was first done by L. Pernille and Mogens N. Olesen in August 1991, at their nursery in Fredensborg, Denmark. This initial and other subsequent propagations conducted in controlled environments have demonstrated that the characteristics of 'POULisab' are true to type and are transmitted from one generation to the next.

BRIEF DESCRIPTION OF THE DRAWING

The accompanying color illustrations shows as true as is reasonably possible to obtain in color photographs of this type, the typical characteristics of the buds, flowers, leaves, and stems of 'POULisab'. Specifically illustrated in SHEET 1:

1. Stem of plant showing branching and the attachment of leaves, buds, and peduncles;

2. Flower bud, partially opened bud, and open bloom;

3. Flower petals, detached.

4. Sepals and pedicel;

5. Flowering stem as well as a bare stem exhibiting thorns;

6. Leaves.

DETAILED DESCRIPTION OF THE VARIETY

The following is a description of 'POULisab', as observed in its outdoor growth in a field nursery in Jackson County, Oreg. Observations were conducted during August, 1991. Color references are made using The Royal Horticultural Society (London, England) Colour Chart, 1995, except where common terms of color are used.

For a comparison, several physical characteristics of the rose variety 'POULman', a Hybrid Tea rose variety, from the same inventors, described and illustrated in U.S. Plant Pat. No. 6,264 and issued on Aug. 30, 1998 is compared to 'POULisab' in Chart 1.

CHART 1

| | 'POULisab' | 'POULari' |
|---|---|---|
| Color of upper surface of petal upon opening. | Red group 53A to 53B. | Red Group 46A–46B. |
| Petalage | Very Double; 55 to 70 petals. | Double; 30 to 35 petals. |
| Fragrance: | Strong. | Slight. |

Parents:

*Seed parent.*—Unnamed seedling.

*Pollen parent.*—'POULnorm'.

Classification:

*Botanical.*—*Rosa hybrida.*

*Commercial.*—Shrub.

FLOWER AND FLOWER BUD

Blooming habit: Nearly continuous.

Flower bud:

*Size.*—Upon opening, 30 to 35 mm in length from base of receptacle to end of bud, with feathered tip extending up tp 20 mm past distal tip of bud.

*Bud form.*—Pointed ovoid with high center.

*Bud color.*—As sepals unfold, Red Group 46A. Red Group 46A at ¼ opening.

*Sepals.*—Green Group 137A and 139A. Moderate foliaceous appendages on three of the five sepals. Sepals on some of the blooms have long, feathered tips extending past the end of the bud. Surfaces of sepals are slightly pubescent. Stipitate glands are present on margins and the outer surface of sepals.

*Receptacle.*—Surface: Smooth, glaucous. Shape: Broadly urn shaped. Size: Medium, 8 mm (h)×8–10 mm (w). Color: Green Group 138B.

*Peduncle.*—Surface: Smooth. Few to no stipitate glands on lower ⅔ of peduncle. Upper ⅓ of peduncle with moderate amount of glands immediately below receptacle. Length: 70 to 90 mm average length. Color: Green Group 138B with strong intonations of Greyed-Purple Group 184A. Strength: Upright.

*Borne.*—Varies from 1 to 4 buds per flowering stem, most commonly with 2 to 4 buds per flowering stem.

Flower bloom:

*Fragrance.*—Moderate to strong with fruity undertones.

*Duration.*—As a cut flower 4 to 6 days. The blooms have a duration on the plant of approximately 5 to 8 days. Petals fall cleanly away from plant.

*Size.*—Medium to large. Average flower diameter is 80 mm when open.

*Form.*—Deep cup. Shape of flower when viewed from the side: Upon opening, upper part: Convex. Upon opening, lower part: Flattened convex. Open flower, upper part: Flat to flattened convex. Open flower, lower part: Flat.

*Petalage.*—Very double. Average range: 55–70 petals under normal conditions with 5–10 petaloids.

Color:

*Upon opening, petals.*—Outermost petals: Upper Surface: Red Group 53A. Reverse Side: Red Group 53B. Innermost petals: Upper Surface: Red Group 46A to 53A. Reverse Side: Red Group 53B.

*Upon opening, basal petal spots.*—Petals: Upper Surface: Yellow Group 7A. Lower Surface: Yellow Group 13B.

*After opening, petals.*—Petals: Upper Surface: Red Group 46A. Reverse Side: Red Group 53B. Innermost petals: Upper Surface: Red Group 46A. Reverse Side: Red Group 53B. Innermost petals show a white variegation in center of petal which is present on both upper and lower surfaces of petal. Occasionally present in ¼ open bud, but much less noticeable.

*After opening, basal petal spots.*—Outermost petals: Upper Surface: Yellow Group 4B. Lower Surface: Yellow Group 4A. Innermost petals: Upper Surface: Yellow Group 4C. Lower Surface: Yellow Group 4B.

General tonality: On open flower Red Group 46A. No change in the general tonality at the end of the $4^{th}$ to $5^{th}$ day. Afterwards, red color lightens slightly.

Petals:

*Petal reflex.*—Petals slightly reflexed.

*Petal edge.*—Slightly undulating with a point in center of margin.

*Shape.*—Deltoid; innermost petals are narrow.

*Petaloids.*—Present. Quantity: 5 to 10.

*Thickness.*—Thick, with a velvety sheen.

*Arrangement.*—Imbricated.

Reproductive organs:

*Pollen.*—Color: Yellow-Orange Group 14C. Quantity: Limited.

*Anthers.*—Size: Medium. Color: Immature: Yellow-Green Group 154C. Quantity: Very abundant.

*Filaments.*—Color: Yellow-Green Group 154C.

*Stigmas.*—Location: Superior in location to anthers. Color: Green-White Group 157A.

*Styles.*—Color: Red-Purple Group 61C.

*Hips.*—None observed.

PLANT

Plant growth: Vigorous and upright. When grown as a budded, field grown plant on *Rosa multiflora* understock. The average height of the plant is 130 cm and the average width is 90 cm.

Stems:

*Color.*—Young wood: Yellow-Green Group 138B with intonations of Greyed-Purple Group 184A. Older wood: Green Group 138B.

*Thorns.*—Incidence: Moderate. Size: Average length: 8 mm. Color: Variable, from Yellow-Green Group 147C to 147D, with intonation of Greyed-Red Group 182C and 182D. Shape: Concave with downward curve.

*Surface.*—Young wood: Smooth. Older wood: Smooth.

*Length.*—80 to 90 cm.

Plant foliage: Typical number of leaflets on leaves in the middle of the stem: 5 leaflets.

*Leaf size.*—Medium, 100–110 mm (l)×85–95 mm (w).

*Abundance.*—Average.

*Color.*—Upper Leaf Surface: Green Group 137A. Lower Leaf Surface: Green Group 138A and 138B. Juvenile foliage: Upper Surface: Green Group 137A and 139A. Lower surface is Green Group 138A. Anthocyanin intonation: Location: Strong anthocyanin intonation on juvenile leaves, rachis, petiole, peduncles, sepals, and stems. Color: Greyed-Red Group 184A.

Plant leaves and leaflets:

*Stipules.*—Size: 18 mm in length. Color: Green Group 143B. Immature stipules have intonations of Greyed-Red Group 184B. Stipitate glands: On margins of stipules.

*Petiole.*—Length: 22 to 24 mm. Color: Green Group 143B. Underneath: Few prickles or glands. Margins: Smooth.

*Rachis.*—Color: Green Group 143B. Underneath: Few prickles or glands. Margins: Limited number of stipitate glands.

*Leaflet.*—Edge: Serrated. Shape: Ovate. Texture: Moderately glossy.

Disease resistance:

Above average resistance to black spot, and Botrytis under normal growing conditions in Jackson County, Oreg.

Cold hardiness: 'POULisab' has been found to be resistant to damage from cold, heat and drought damage in USDA Zone 7.

We claim:

1. A new and distinct variety of rose plant of the shrub class, substantially as herein illustrated and described as a distinct and novel rose variety due to its abundant, dark red flowers, vigorous growth, disease resistance, and extended period of bloom.

* * * * *

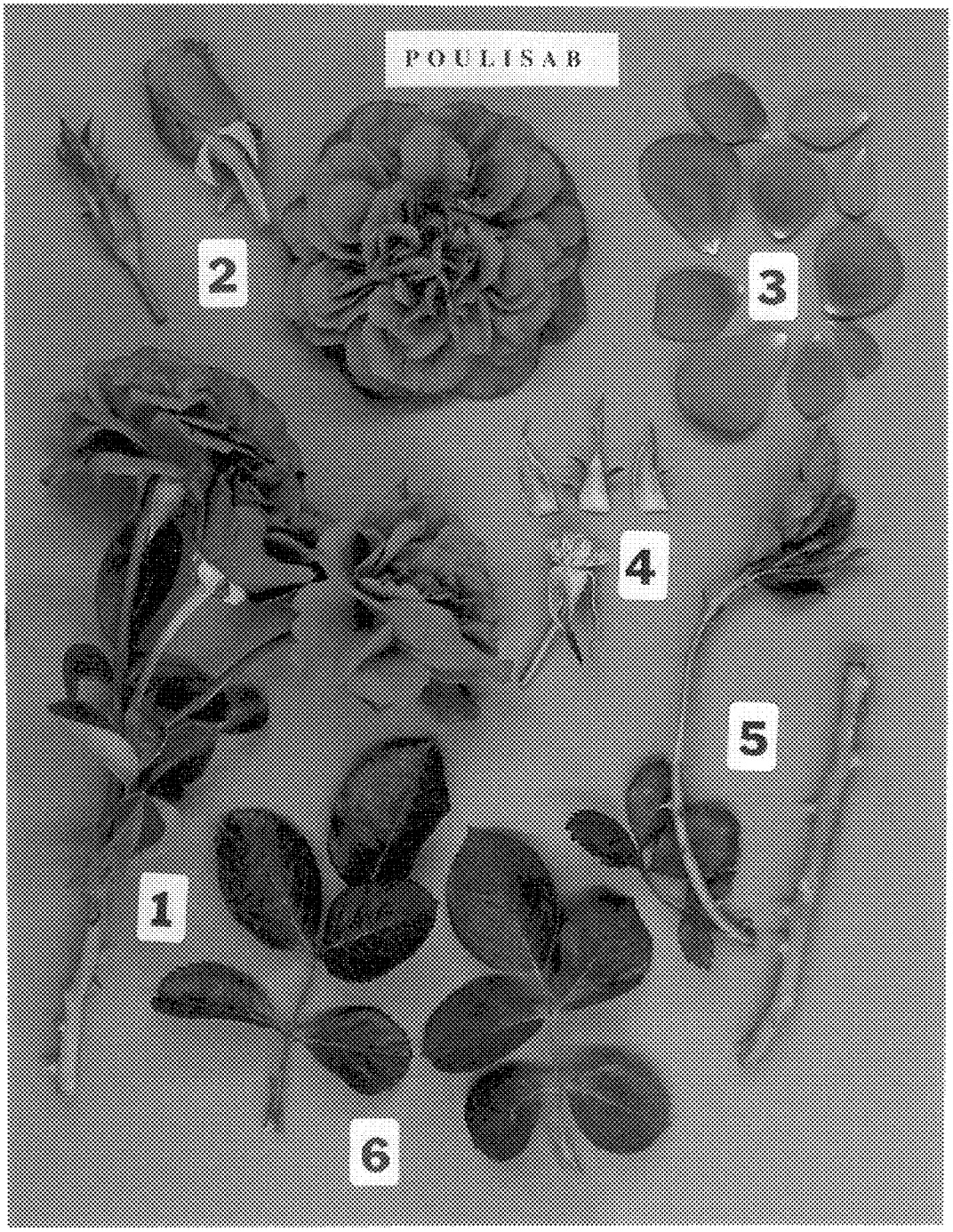
POULISAB
2
3
4
5
1
6